United States Patent
Chung et al.

(10) Patent No.: US 12,201,559 B2
(45) Date of Patent: Jan. 21, 2025

(54) MEDICAL VACUUM TWEEZER AND TISSUE SUTURING DEVICE INCLUDING THE SAME

(71) Applicants: POSTECH Research and Business Development Foundation, Pohang-si (KR); Kyungpook National University Industry-Academic Cooperation Foundation, Daegu (KR)

(72) Inventors: Wan Kyun Chung, Pohang-si (KR); Ikjong Park, Iksan-si (KR); Hong Kyun Kim, Daegu (KR); Hyung Gon Shin, Seoul (KR)

(73) Assignees: POSTECH RESEARCH AND BUSINESS DEVELOPMENT FOUNDATION, Pohang-si (KR); KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 382 days.

(21) Appl. No.: 17/477,658

(22) Filed: Sep. 17, 2021

(65) Prior Publication Data

US 2022/0110788 A1    Apr. 14, 2022

(30) Foreign Application Priority Data

Oct. 13, 2020  (KR) .................. 10-2020-0132173

(51) Int. Cl.
*A61F 9/007*    (2006.01)
(52) U.S. Cl.
CPC .................. *A61F 9/007* (2013.01)

(58) Field of Classification Search
CPC .. A61F 9/007; A61F 9/00736; A61B 17/0482; A61B 90/50; A61B 17/30; A61B 2017/306; A61B 17/0231; A61B 17/06066; A61B 2017/00561; A61B 2017/0608; A61B 2017/305; A61B 17/06; A61B 17/0467; A61B 17/50; A61B 17/28; A61B 17/29; A61B 17/0469; A61B 17/0491;
(Continued)

(56) References Cited

U.S. PATENT DOCUMENTS 7,147,648 B2    12/2006  Lin
7,810,814 B1 *  10/2010  Chapman ............ A63F 3/00094
                                                    273/287

(Continued)

FOREIGN PATENT DOCUMENTS

KR    10-1989-0014060    10/1989
KR    10-1661452         10/2016
(Continued)

*Primary Examiner* — Phong Son H Dang
*Assistant Examiner* — Andrew P. Restaino
(74) *Attorney, Agent, or Firm* — LEX IP MEISTER, PLLC

(57) ABSTRACT

A vacuum tweezer according to the present disclosure includes: a first plate and a second plate of which first and second needle holes facing each other are drilled at lower ends of each, and are positioned to face each other; and a first side plate and a second side plate connecting and fixing the first plate and second plate to form a tube and including a recess portion that is concave downward at a higher position than the first and second needle holes, respectively.

11 Claims, 15 Drawing Sheets

(58) Field of Classification Search
CPC ............ A61B 17/06061; A61B 17/062; A61B 17/0625
See application file for complete search history.

(56) References Cited

U.S. PATENT DOCUMENTS

| | | |
|---|---|---|
| 7,862,572 B2 | 1/2011 | Meade et al. |
| 2005/0010243 A1 | 1/2005 | Lin |
| 2007/0219571 A1* | 9/2007 | Balbierz ............... A61F 5/0036 606/153 |
| 2010/0137888 A1* | 6/2010 | Wulc ................. A61B 17/0625 606/144 |
| 2012/0130389 A1 | 5/2012 | Prywes |
| 2015/0045817 A1* | 2/2015 | Li ..................... A61B 17/0469 606/148 |

FOREIGN PATENT DOCUMENTS

| | | |
|---|---|---|
| KR | 10-2017-0102718 | 9/2017 |
| KR | 10-2017-0130819 | 11/2017 |
| KR | 10-1811943 | 12/2017 |
| KR | 10-2019-0030499 | 3/2019 |

* cited by examiner

Donor cornea

MEDICAL VACUUM TWEEZER AND TISSUE SUTURING DEVICE INCLUDING THE SAME

CROSS-REFERENCE TO RELATED APPLICATION

This application claims priority to and the benefit of Korean Patent Application No. 10-2020-0132173 filed in the Korean Intellectual Property Office on Oct. 13, 2020, the entire contents of which are incorporated herein by reference.

BACKGROUND OF THE INVENTION

(a) Field of the Invention

The present invention relates to a medical tweezer capable of gripping a body tissue and a tissue suturing device including the same.

(b) Description of the Related Art

As a device for suturing during a medical surgery, medical forceps and suturing needles capable of gripping a tissue are generally used. When wound suturing is performed during the medical surgery, different types of suturing are required depending on types and shapes of the wound. The suturing shape may be defined as a trajectory of the suturing thread left after the needle has passed through the tissue. Therefore, for accurate suturing shape control, it is important to continuously understand the path through which the point of the needle tip moves inside the tissue during the process of penetrating the tissue until the needle is inserted into the tissue and then withdrawn.

However, in controlling the shape of the suturing using the existing suturing device, the inside of the tissue cannot be observed while the needle is passing through the tissue, so a method relying solely on intuition to infer the relative position of the tip of the needle inside the tissue and adjusting the position of the needle according thereto is applied. Therefore, on the point that the suturing shape control using the existing suturing device depends on intuition, there are limits in accurate suturing prediction and control. In addition, there is a limitation in that it is difficult to accurately adjust the needle position because the user's hand tremor vibration is transmitted to the needle as it is.

On the other hand, in a case of corneal suturing in an ophthalmic surgery, the shape of the suturing greatly affects surgical prognosis, so that reoperation may need to be performed due to a wrong shape of the suturing. For example, if the suturing depth is too large, the cornea may be punctured and a foreign material may enter the eye. Alternatively, if the suturing length is too short, eye fluid leakage may occur in the suturing part. Also, if the shape of the suturing is not uniform, a severe astigmatism may occur. Therefore, a technique capable of accurately controlling the shape of the suturing, that is, the suturing depth and the length, is required during the wound suturing including the corneal surgery.

Patent Document 1 (U.S. Pat. No. 7,862,572 B2) proposes an automatic suturing device for uniform suturing, but since it is a suturing device for laparoscopic surgery, the size thereof is large and the shape of the suturing is limited.

In order to solve the problem of the accuracy of the suturing in ophthalmic surgery, Patent Document 2 (U.S. Pat. No. 7,147,648 B2) proposes a device for fixing the tissue using a vacuum pressure. However, since it was developed specifically for the cornea, it is difficult to be used for a general micro suturing, it may interfere with the operator's field of vision by fixing the entire cornea, and there is a possibility of tissue damage by a vacuum pressure as the adsorption area is wide. Therefore, a device that can fix only a part of the tissue is required.

The above information disclosed in this Background section is only for enhancement of understanding of the background of the invention, and therefore it may contain information that does not form the prior art that is already known in this country to a person of ordinary skill in the art.

SUMMARY OF THE INVENTION

One aspect of the present invention is to provide a vacuum tweezer that can perform suturing with a target length and depth when suturing a fine wound, and can always perform uniformly shaped suturing even after multiple suturing, and a tissue suturing device including the same.

Objects to be solved by the embodiments of the present invention are not limited to the above-mentioned objects, and can be variously extended within the scope of the technical idea included in the present invention.

A vacuum tweezer according to an exemplary embodiment of the present invention includes a first plate and a second plate of which first and second needle holes facing each other are drilled at lower ends of each, and are positioned to face each other; and a first side plate and a second side plate connecting and fixing the first plate and the second plate to form a tube and including a recess portion that is concave downward at a higher position than the first and second needle holes, respectively.

At least one third side plate positioned between the first side plate and the second side plate, connecting and fixing the first plate and the second plate, and including a recess portion that is concave downward at a higher position than the first and second needle holes may be further included.

Each recess portion of the first side plate, the second side plate, and the third side plate may include a needle path line connecting the facing first and second needle holes, and may be configured to have a profile of the same height with respect to an imaginary plane perpendicular to the first side plate, the second side plate, and the third side plate.

Each recess portion of the first side plate and the second side plate may include a needle path line connecting the facing first and second needle holes and be configured to have a profile of the same height with respect to an imaginary plane perpendicular to the first side plate and the second side plate.

Each recess portion of the first side plate and the second side plate may be formed to deepen upward in a direction away from each of the first and second plates.

A deepest vertex of the recess portion may be positioned closer to the second plate than the first plate.

The length by which the second plate extends downward from the center of the second needle hole may be formed longer than the length by which the first plate extends downward from the center of the first needle hole.

The second plate may have a cutout part extending downward from the second needle hole.

The width of the cutout part may be formed smaller than the diameter of the second needle hole.

The first plate may have a cutout part extending downward from the first needle hole.

The width of the cutout part may be formed smaller than the diameter of the first needle hole.

A third plate having a third needle hole drilled facing the second needle hole at the lower part, and positioned to face the second plate; and a fourth side plate and a fifth side plate connecting and fixing the second plate and the third plate to form a tube and including a recess portion that is concave downward at the higher position than the second and the third needle hole at the lower part may be further included.

A vacuum tweezer according to another exemplary embodiment of the present invention as a vacuum tweezer including a body member including a first end and a second end positioned on sides opposite to each other and extending long, wherein the body member has a tube shape through which the inside is penetrated in the length direction, a first needle hole and a second needle hole opposite to each other are formed in the portion adjacent to the first end, and a lateral recess portion formed by cutting out the body member further inside than the imaginary needle path line connecting the first needle hole and the second needle hole is further included.

The lateral recess portion may include a first lateral recess portion and a second lateral recess portion including the needle path line and symmetrical with respect to an imaginary plane extending in a length direction of the body member.

At least one middle side plate extending in the length direction of the body member inside the body member may be further provided, and the middle side plate may include a middle recess portion having the same depth as the lateral recess portion.

The lateral recess portion may be positioned closer to at least one of the first needle hole or the second needle hole than the other.

A tissue suturing device according to another exemplary embodiment of the present invention includes: the vacuum tweezer as above-described, a needle insertion unit fixed adjacent to one of the first needle hole or the second needle hole of the vacuum tweezer to drive the suturing needle; and a negative pressure generating unit connected to the upper part of the vacuum tweezer to provide suction power.

According to the vacuum tweezer and the tissue suturing device including the same according to an exemplary embodiment of the present invention, the suturing having a target length and depth when suturing a micro wound may be performed, and sutures of a uniform shape may always be formed even during multiple suturing.

In addition, it is possible to control the moving path when the needle passes through the tissue by the contact portion of the vacuum tweezer attached to the wound surface by negative pressure, so the shape of the suturing may be finely adjusted without hand tremors or errors due to inexperienced skills.

DETAILED DESCRIPTION OF THE EMBODIMENTS

Figure 1:
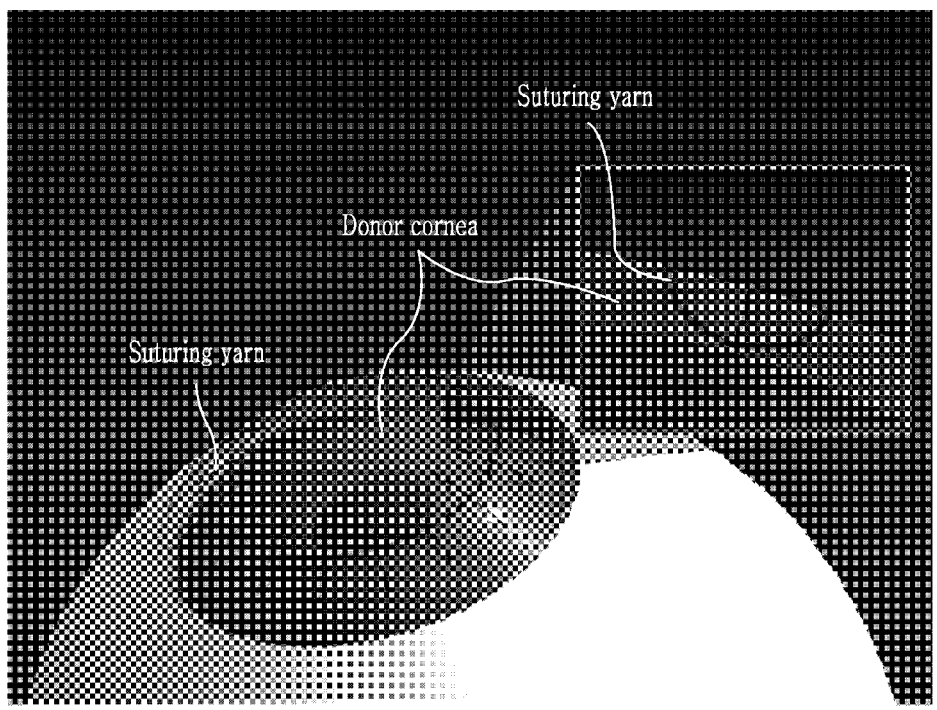
FIG. 1 is a photographic image to explain a corneal suturing process.

The present invention will be described more fully hereinafter with reference to the accompanying drawings, in which exemplary embodiments of the invention are shown. The drawings and description are to be regarded as illustrative in nature and not restrictive. Like reference numerals designate like elements throughout the specification. The accompanying drawings are provided only in order to allow exemplary embodiments disclosed in the present specification to be easily understood and are not to be interpreted as limiting the spirit disclosed in the present specification, and it is to be understood that the present invention includes all modifications, equivalents, and substitutions without departing from the scope and spirit of the present invention.

Terms including ordinal numbers such as first, second, and the like will be used only to describe various components, and are not to be interpreted as limiting these components. The terms are only used to differentiate one component from other components.

It is to be understood that when one component is referred to as being "connected" or "coupled" to another component, it may be connected or coupled directly to the other component or may be connected or coupled to the other component with a further component intervening therebetween. Further, it is to be understood that when one component is referred to as being "directly connected" or "directly coupled" to another component, it may be connected or coupled directly to the other component without a further component intervening therebetween.

In this application, it should be understood that the terms such as "comprises" or "having" are to specify the presence of features, numbers, steps, operations, constituent elements, parts, or any combination of them described in the specification, but it does not preclude the possibility of the presence or addition of one or more other features, numbers, steps, operations, constituent elements, parts, or any combination of them. Accordingly, unless explicitly described to the contrary, the word "comprise" and variations such as "comprises" or "comprising" will be understood to imply the inclusion of stated elements but not the exclusion of any other elements.

FIG. 1 is a photographic image to explain a corneal suturing process.

As a final treatment method of a corneal treatment that improves deterioration of vision due to turbidity or refractive error of a cornea and does not respond to other treatments, corneal transplantation is used. The corneal transplantation is an operation in which a recipient cornea is excised from a transplant recipient, and then a donor cornea is collected from a transplant donor according to the size and the suturing is executed.

Referring to FIG. 1, it is common that the patient's corneal part from which the recipient cornea has been resected and the donor cornea have a circular inner edge and a circular outer edge, respectively. Therefore, in order to suture the donor cornea to the patient, the suturing is performed while forming a plurality of suturing loops using a suturing needle and suturing yarn along the circular edges. Here, each suturing loop may have a suturing trajectory such that it is inserted from the surface of the donor cornea and drawn out to the surface of the patient's cornea through the boundary surface when observed on the cross-section of the cornea.

Figure 2:
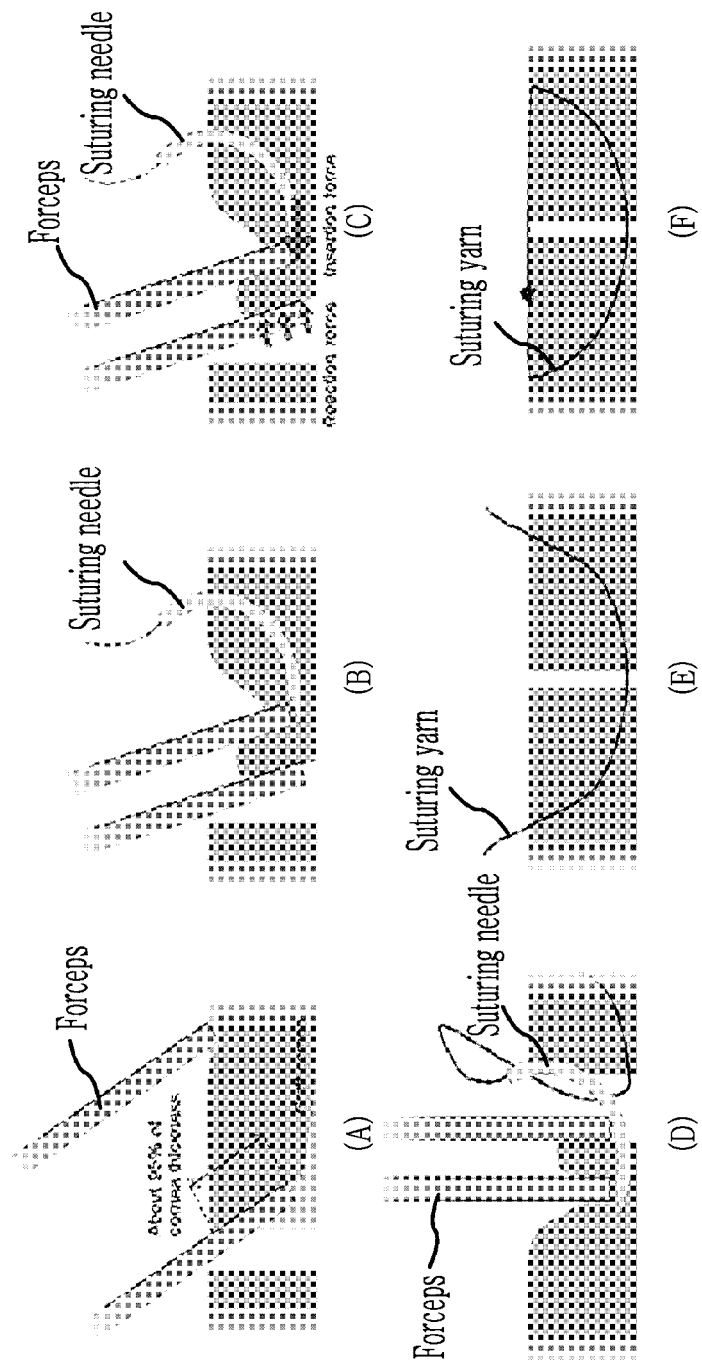
FIG. 2 is a flowchart to schematically explain a corneal suturing process using a conventional suturing tool.

FIG. 2 is a flowchart to schematically explain a corneal suturing process using a conventional suturing tool.

Referring to FIG. 2, in the corneal suturing process, one side of the donor cornea or the patient cornea is held and fixed by using medical forceps, etc. (referring to FIG. 2(A)), and in this state, the suturing needle is pierced in the thickness direction of the cornea from the surface of the cornea to move the suturing yarn (referring to FIGS. 2(B) and (C)). Then, the other side of the donor cornea or patient cornea is held by using medical forceps to be fixed (referring to FIG. (D)), and the suturing needle that passed through the one side is pierced in the thickness direction of the cornea from the cornea side of the other side to the surface of the cornea to move the suturing yarn (referring to FIG. 2(E)). Thereby, the patient cornea and donor cornea are connected to each other by the suturing yarn, and the suturing yarn is fixed by knotting on the surface of the cornea (referring to FIG. 2(F)).

By repeating the above process several times along the circular rim of the donor cornea, the donor cornea may be sutured into the patient cornea, thereby completing the same form as shown in FIG. 1.

Figure 3:
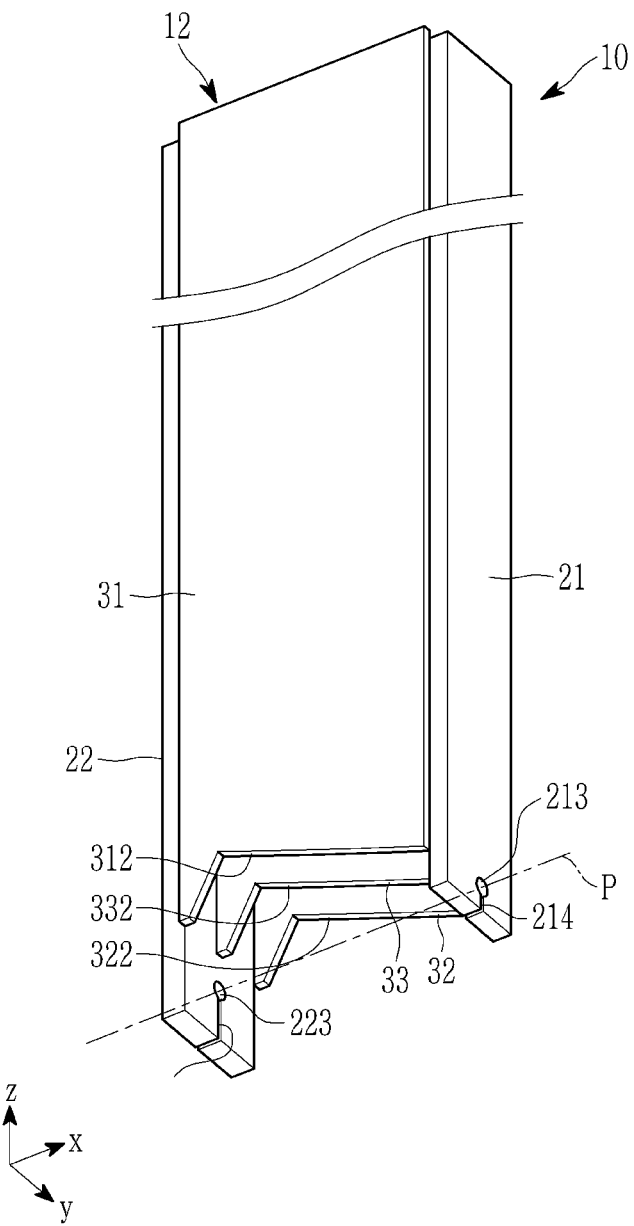
FIG. 3 is a perspective view showing a vacuum tweezer according to an exemplary embodiment of the present invention.
Figure 4A:
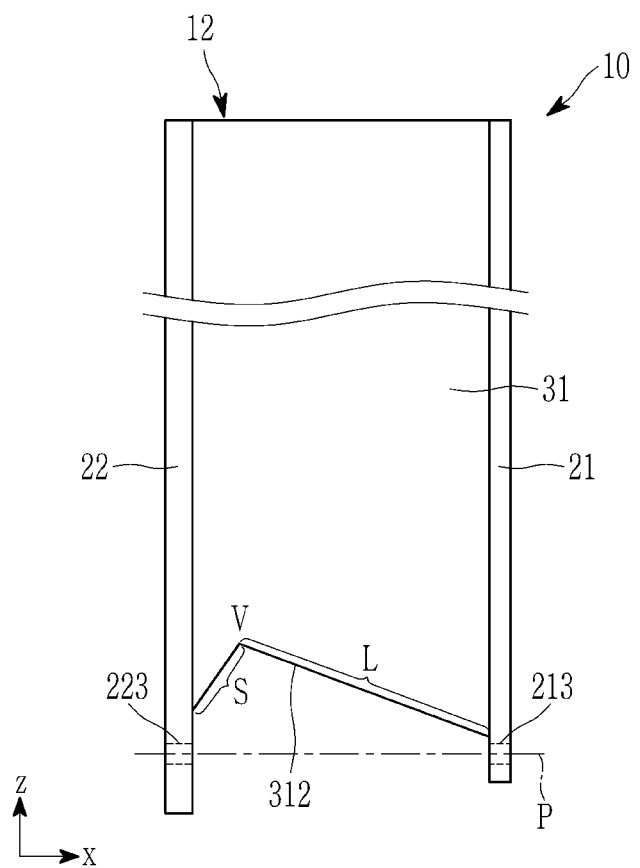
FIG. 4A is a front view showing a vacuum tweezer according to an exemplary embodiment of the present invention.
Figure 4B:
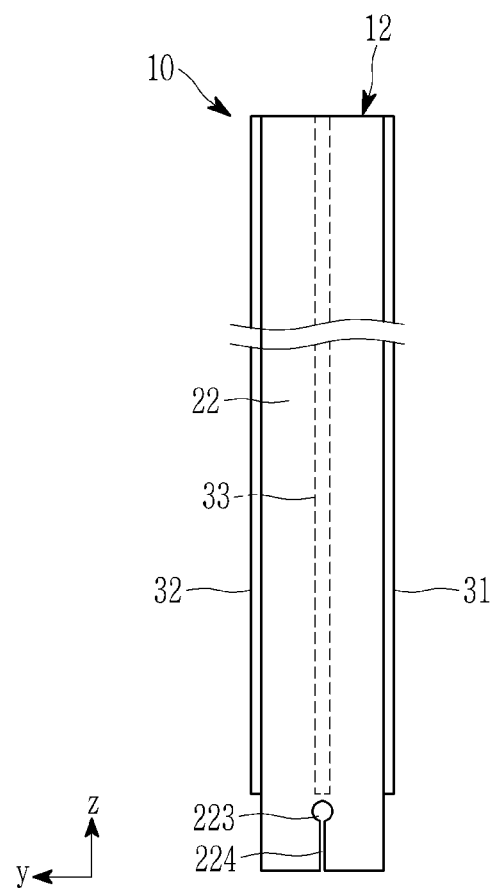
FIG. 4B is a left side view.

FIG. 3 is a perspective view showing a vacuum tweezer according to an exemplary embodiment of the present invention, FIG. 4A is a front view showing a vacuum tweezer according to an exemplary embodiment of the present invention, FIG. 4B is a left side view.

The vacuum tweezer 10 according to the present exemplary embodiment includes a body member 12 formed in a form of a tube having the inside penetrated in the length direction. One end of the body member 12 may be configured as a contact end and the other end may be configured as a connecting end. The contact end is a part in contact with the wound tissue to be sutured, and the connection end is a part connected to a negative pressure generating unit (not shown) that generates a negative pressure. The contact end may be attached to the surface of the wound tissue to be sutured by using the negative pressure, and the tissue may be deformed into a predetermined specific shape in advance. A needle hole is also formed at the contact end so that a suturing needle may be inserted in a predetermined direction into the tissue deformed by the contact portion.

Referring to FIG. 3, the vacuum tweezer 10 according to the present exemplary embodiment may include a body member 12 in the form of a rectangular tube. That is, the vacuum tweezer 10 includes a first plate 21 and a second plate 22 positioned to face each other, and a first side plate 31 and a second side plate 32 that are fixed to connect the first plate 21 and the second plate 22 to form a tube. The first plate 21 and the second plate 22 may be disposed parallel to each other and extended in the same direction (the z-axis direction of the drawing). The first side plate 31 and the second side plate 32 are also disposed parallel to each other and extended in the same direction (the z-axis direction of the drawing), and may be vertically disposed with respect to the first plate 21 and the second plate 22. A third side plate 33 connecting the first plate 21 and the second plate 22 to be fixed may be positioned between the first side plate 31 and the second side plate 32, and the third side plate 33 may be positioned vertically with respect to the first plate 21 and second plate 22.

The first plate 21 and the second plate 22 have a first needle hole 213 and a second needle hole 223 that are penetrated to correspond to each other at the lower end, that is, the part adjacent to the contact end. Each of the first side plate 31 and the second side plate 32 may be formed with a recess portion 312 and 322 concave downward to the contact end, and the recess portion 312 and 322 may be formed at a higher position than the needle holes 213 and 223. That is, the recess portions 312 and 322 may be formed as the first side plate 31 and the second side plate 32 and are cut out upwards based on the imaginary needle path line P connecting the first needle hole 213 and the second needle hole 223. A recess portion 332 that is concave downward at the higher position than the needle holes 213 and 223 may also be formed on the contact end of the third side plate 33.

Each of the recess portions 312 and 322 of the first side plate 31 and the second side plate 32 may be configured to have a profile of the same height with respect to an imaginary plane including the needle path line P and perpendicular to the first side plate 31 and the second side plate 32. In addition, the recess portion 332 of the third side plate 33 may also be configured to have a profile of the same height as each of the recess portions 312 and 322 of the first side plate 31 and the second side plate 32 with respect to the imaginary plane.

Referring to FIG. 4A, the recess portion 312 of the first side plate 31 deepens upward in the direction away from each of the first plate 21 and the second plate 22, and the deepest vertex V of the recess portion 312 may be positioned to slant closer to the second plate 22 than the first plate 21. Therefore, the recess portion 312 may include a short side S extending from the vertex V to the second plate 22 and a long side L extending from the vertex to the first plate 21.

Also, as described above, when each of the recess portions 322 and 332 of the second side plate 32 and the third side plate 33 also have the same profile as the first side plate 31, the recess portions 322 and 332 of the second side plate 32 and the third side plate 33 also deepen upward in the direction away from each of the first plate 21 and the second plate 22, and the deepest vertex V of the recess portions 322 and 332 may be positioned to slant closer to the second plate 22 than the first plate 21.

As above-described, when the deepest vertex V of the recess portions 312, 322, and 332 is disposed closer to the second plate 22 than the first plate 21, the vertex part of the cornea (i.e., the corner part that borders the side surface and the upper surface) may be induced to be positioned in the vertex V part.

Also, the second plate 22 may be configured to extend further down from the center of the needle hole than the first plate 21.

As above-described, when the second plate 22 is configured to extend further down from the center of the needle hole than the first plate 21, in the process of aligning the second plate 22 with the corneal incision prior to a vacuum suction, the alignment may be easier.

Referring to FIG. 4B, the second plate 22 may have a cutout part 224 extending downward from the second needle hole 223. Likewise, the first plate 21 may have a cutout part 214 extending downward from the first needle hole 213 (referring to FIG. 3). Here, the width of the cutout parts 214 and 224 may be formed smaller than the diameter of the needle holes 213 and 223. The cutout parts 214 and 224 may be provided so that the suturing needle N passes through the needle holes 213 and 223, and then the suturing yarn T is easily removed through this when the vacuum tweezer 10 is separated from the tissue.

The contact end of the body member 12 of the vacuum tweezer 10 configured in this way is attached to the surface of the wound tissue by a negative pressure, and at this time, the deformation of the wound tissue may be induced by the shape of the recess portions 312, 322, and 332 of the first, second, and third side plates 31, 32, and 33.

Figure 5:
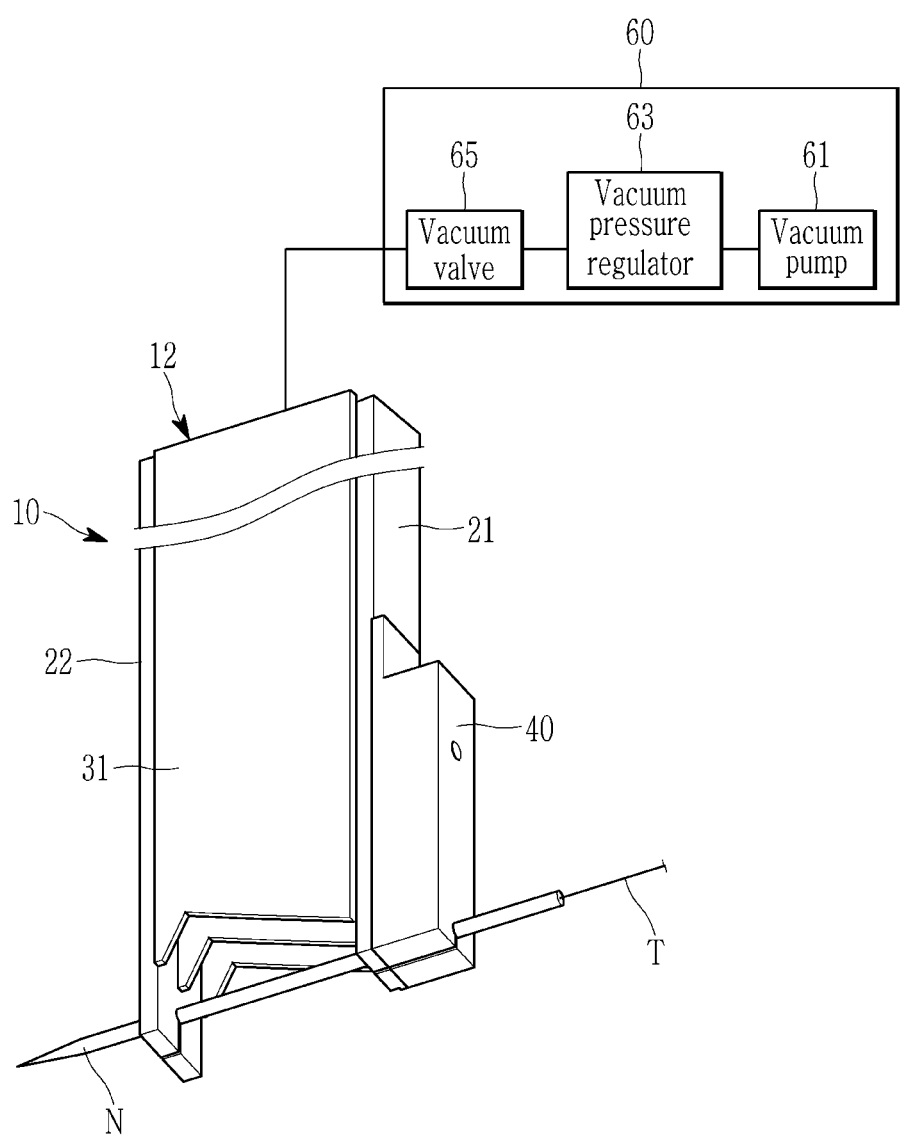
FIG. 5 is a perspective view showing a state in which a needle insertion unit is mounted on a vacuum tweezer according to an exemplary embodiment of the present invention.

FIG. 5 is a perspective view showing a state in which a needle insertion unit is mounted on a vacuum tweezer according to an exemplary embodiment of the present invention.

Referring to FIG. 5, the needle insertion unit 40 may be fixed adjacent to the first needle hole 213 of the body member 12 of the vacuum tweezer 10. That is, the needle insertion unit 40 may be supported and fixed to the first plate 21 in which the first needle hole 213 is formed.

The vacuum tweezer 10 may set an imaginary needle path line P (referring to FIG. 3) along the extension line connecting the first needle hole 213 formed on the first plate 21 and the second needle hole 223 formed on the second plate 22. The needle insertion unit 40 may drive the suturing needle N by fixing the direction so that the suturing needle N moves without shaking along the needle path line P. Here, the suturing needle N may be a straight line type of needle.

The needle insertion unit 40 may be driven and guided so that the suturing needle N is always inserted in a uniform direction when the suturing needle N is inserted into the tissue deformed by the contact end of the vacuum tweezer 10. The needle insertion unit 40 may be perforated to maintain the insertion direction of the needle.

However, the present invention is not limited thereto, and the needle insertion unit 40 may be fixed adjacent to the second needle hole 223 of the body member 12 of the vacuum tweezer 10. That is, the needle insertion unit 40 may be supported and fixed to the second plate 22 in which the second needle hole 223 is formed, which is also within the scope of the present invention.

The vacuum tweezer 10 has an upper end that is connected to the negative pressure generating unit 60, thereby receiving suction power. The negative pressure generating unit 60 may include, for example, a vacuum pump 61, a vacuum pressure regulator 63, and a vacuum valve 65. The vacuum pump 61 may generate a vacuum, and the vacuum pressure regulator 63 is connected to between the vacuum pump 61 and the vacuum tweezer 10 so that the vacuum pressure may be adjusted to the most appropriate level so as to not damage the tissue. Also, the vacuum valve 65 is connected between the vacuum pressure regulator 63 and the vacuum tweezer 10 to control an opening/closing (on/off) of the vacuum pressure.

As another example, the negative pressure generating unit 60 may include a syringe (not shown) equipped with a spring, and if the syringe is connected to the top of the body member of the vacuum tweezer 10, when the vacuum tweezer 10 touches the tissue, the spring operates to generate a vacuum.

FIG. 6A to FIG. 6E are schematic flowcharts illustrating a corneal suturing process using a vacuum tweezer according to an exemplary embodiment of the present invention.

According to the shape of the contact end recess portions 312, 322, and 332 of the first side plate 31, the second side plate 32, and the third side plate 33 of the vacuum tweezer 10, it is possible to induce a temporary deformation of the wound tissue in contact therewith. The contact end recess portion 312 of the first side plate 31 has the deepest vertex V, and the width W in the horizontal direction and the height H from the lower end of the first plate 21 to the vertex V may be appropriately set according to the suturing target. At this time, the vertex V of the contact end recess portion 312 may be positioned closer to the second plate 22 than the first plate 21.

When the vacuum tweezer 10 is attached to the tissue using negative pressure, the wound tissue may fill and be in contact with the contact end recess portions 312, 322, and 332 of the first side plate 31, the second side plate 32, and the third side plate 33. Accordingly, the recess portions 312, 322, and 332 of the side plates 31, 32, and 33 determine the deformed shape of the tissue. According to the deformed shape of the tissue, the path through which the suturing needle passes inside the tissue may be determined, and the suturing shape may be resultantly determined. The shape of the suturing may be adjusted by adjusting the width W and the height H of the recess portions 312, 322, and 332 and determining the position of the vertex V.

Figure 6A:
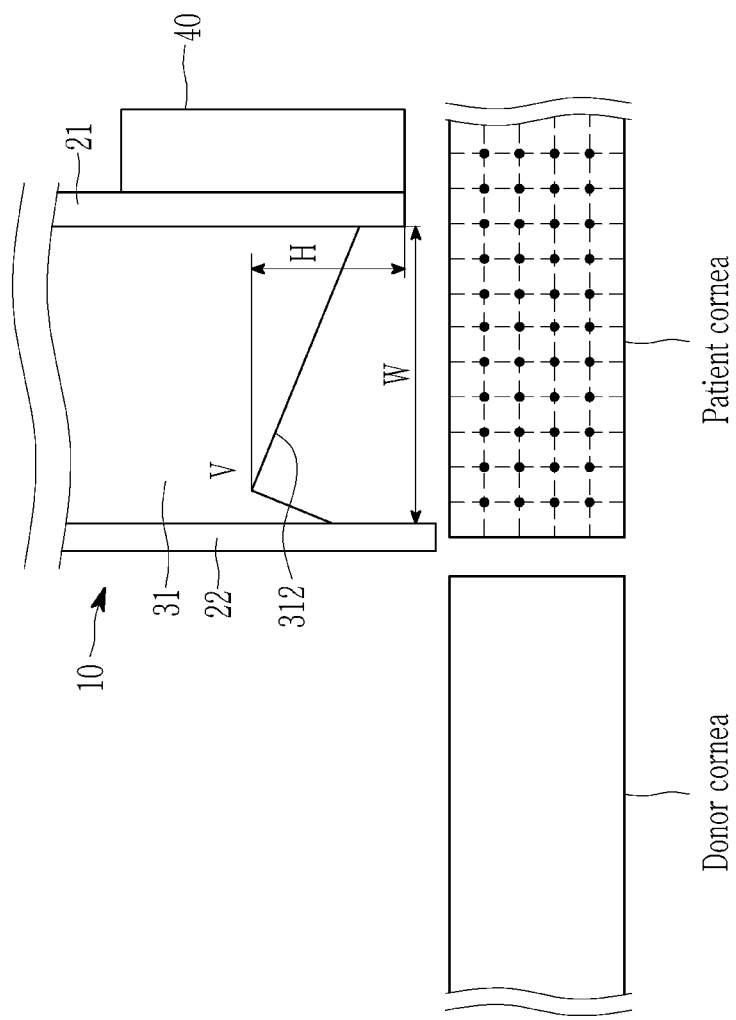
FIG. 6A to FIG. 6E are schematic flowcharts illustrating a corneal suturing process using a vacuum tweezer according to an exemplary embodiment of the present invention.

Referring to FIG. 6A, first, the vacuum tweezer 10 is positioned so that the boundary surface of the donor cornea, which is the suturing surface, is roughly aligned with the second plate 22. In the recess portion 312 of the vacuum tweezer 10, the deepest vertex V is positioned to be slanted closer to the second plate 22 than the first plate 21, so the boundary surface of the donor cornea, which is the suturing surface, is positioned close to the vertex V. Since the suturing needle needs to be inserted from the surface of the donor cornea, the part to insert the suturing needle (i.e., the area close to the center of the donor cornea) is positioned on the first plate 21 side of the vacuum tweezer 10.

FIG. 6A schematically shows the parts of the cross-section of the patient cornea and the donor cornea, and they are disposed so that the boundary surfaces of the donor cornea and the patient cornea to be joined are adjacent to each other. The donor cornea is shown with lattice-type coordinate points so that the deformed state may be easily identified during the suturing process.

Figure 6B:
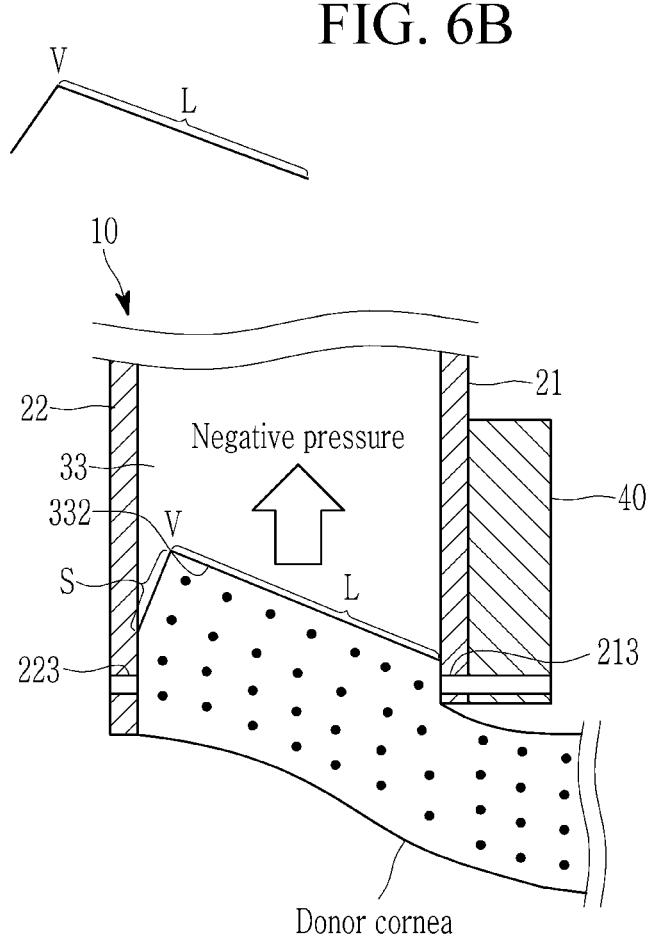

Referring to FIG. 6B, when the negative pressure generating unit (not shown) connected to the connection end of the vacuum tweezer 10 is driven to generate the negative pressure in the body member 12 of the vacuum tweezer 10, the boundary surface and part of the surface of the donor cornea contacted to the contact end may be adsorbed by filling the recess portion 312. That is, the boundary surface of the donor cornea is in contact with the short side S positioned to the left of the vertex V of the recess portion 312, and the surface of the donor cornea is in contact with the long side L positioned to the right of the vertex V of the recess portion 312.

Figure 6C:
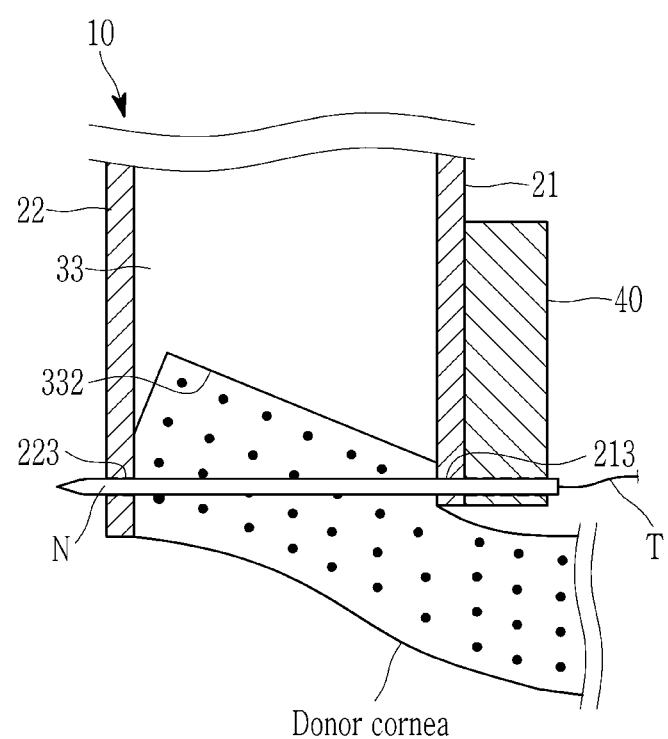

Referring to FIG. 6C, in the state that the vacuum tweezer 10 adsorbs the boundary surface and the part of the surface of the donor cornea into the recess portion 312, the suturing needle N passes through the donor cornea. The suturing needle N is inserted through the first needle hole 213 of the first plate 21 by driving the needle insertion unit 40 attached to the first plate 21 of the vacuum tweezer 10, and then the suturing needle N is continuously advanced to penetrate the donor cornea and then to be drawn out through the second needle hole 223 of the second plate 22.

Figure 6D:
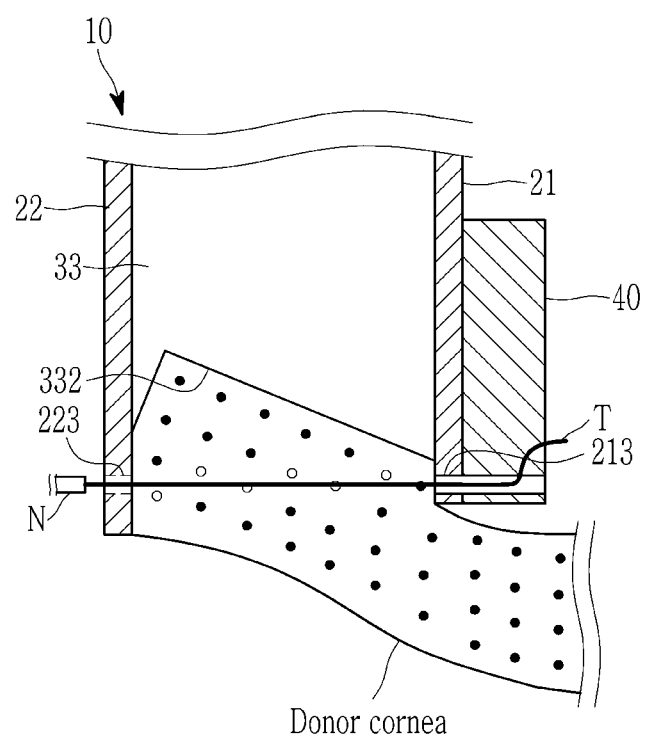

Referring to FIG. 6D, the suturing yarn T is connected to the rear end of the suturing needle N, moves along the movement path of the suturing needle N as the suturing needle N moves, and then is inserted and fixed along the suturing trajectory inside the donor cornea.

Figure 6E:
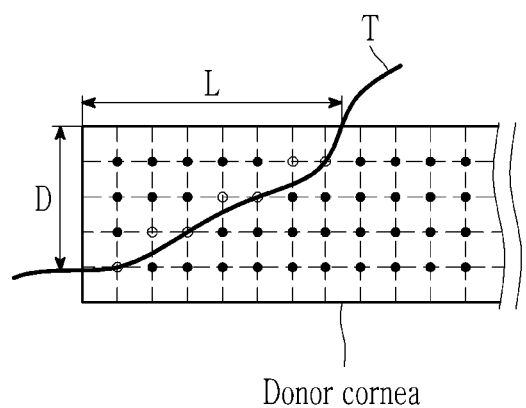

FIG. 6E shows the state in which the donor cornea is separated from the vacuum tweezer 10 by releasing the negative pressure inside the body member 12 of the vacuum tweezer 10 after the suturing yarn T is passed through the suturing needle N and inserted along the suturing trajectory. The separated donor cornea is restored to the original shape thereof, and accordingly, the suturing trajectory of the suturing yarn T forms an approximately left-downward trajectory from the surface of the donor cornea to the boundary surface.

On the other hand, for the patient cornea, by using a vacuum tweezer and a needle insertion unit with a structure symmetrical to the vacuum tweezer 10 of the above structure, the suturing needle may be inserted into the boundary surface of the patient cornea, and the suturing needle may be draw out into the surface of the patient cornea. Thereby, the suturing needle that has passed through the donor cornea is inserted and passed into the patient cornea, and accordingly, the suturing trajectory may be formed in the donor cornea, and the suturing trajectory may be formed so that the fixed suturing yarn is continuous to the patient's cornea. Finally, the suturing loop may be completed by knotting the suturing yarn drawn out on each surface of the donor cornea and the patient cornea.

Also, as another example, the suturing needle is inserted into the surface of the patient cornea, the suturing needle is draw out to the boundary surface of the patient cornea, the suturing needle is inserted into the boundary surface of the donor cornea, and the suturing needle is draw out to the surface of the donor cornea, thereby it is also possible to form the suturing trajectory.

Figure 7:
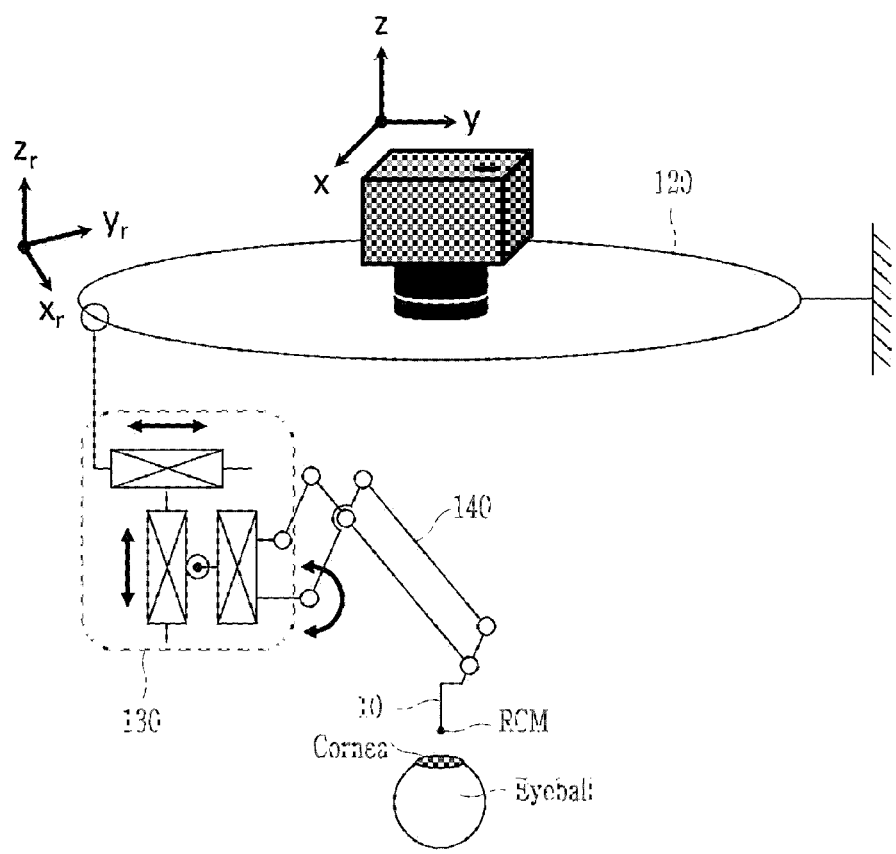
FIG. 7 is a schematic diagram schematically showing a robot arm tissue suturing system including a vacuum tweezer according to an exemplary embodiment of the present invention.

FIG. 7 is a schematic diagram schematically sowing a robot arm tissue suturing system including a vacuum tweezer according to an exemplary embodiment of the present invention.

The vacuum tweezer 10 according to the present exemplary embodiment may be used by being mounted on an automated robot arm suturing device.

Referring to FIG. 7, the robot arm suturing device includes a four-bar linkage 140 fixed by the vacuum tweezer 10, an XYZ linear stage 130 to which one end of the four-bar linkage 140 is fixed, and a rotary stage 120 to which one end of the XYZ linear stage 130 is fixed. The rotary stage 120 may be held and fixed to a stable fixed base frame (not shown).

The four-bar linkage 140 may be operated to set the end point of the lower end of the vacuum tweezer 10 as a remote center of motion (RCM) point and to rotate around it. The XYZ linear stage 130 may control the position while moving in the three-axis direction of the four-bar linkage 140. In addition, the rotary stage 120 may control the position while rotating and driving the XYZ linear stage 130 about the central axis.

Figure 8:
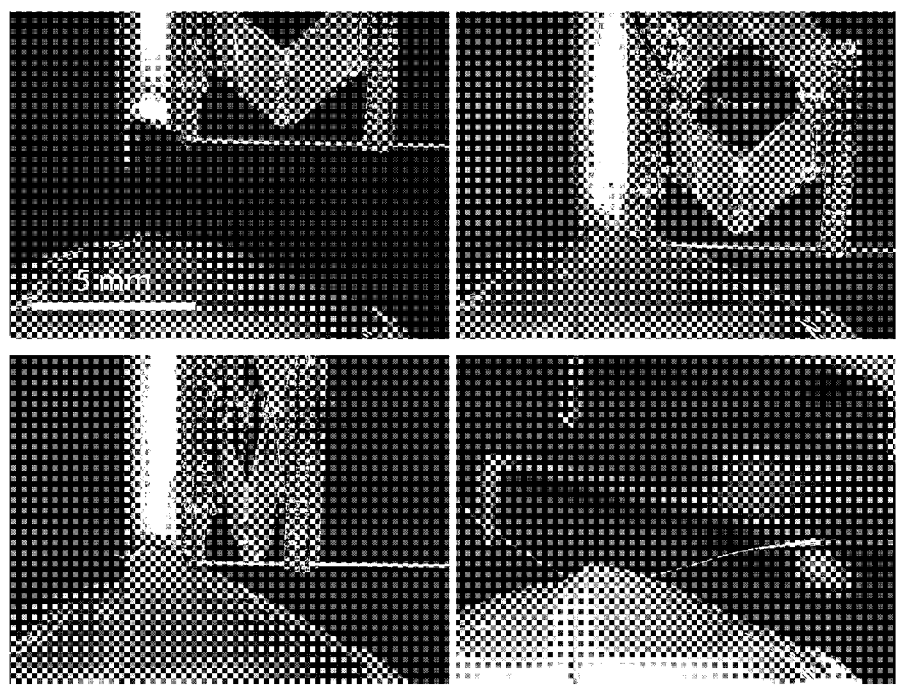
FIG. 8 is a photographic image showing a corneal suturing process using a tissue suturing device including a vacuum tweezer according to an exemplary embodiment of the present invention.

FIG. 8 is a photographic image showing a corneal suturing process using a tissue suturing device including a vacuum tweezer according to an exemplary embodiment of the present invention.

Referring to FIG. 8, the vacuum tweezer 10 to which the needle insertion unit 40 is mounted is positioned close to the donor cornea (referring to an upper-left image), the vacuum tweezer 10 is positioned to be in contact with the donor cornea, and the negative pressure is generated, thereby the donor cornea is adsorbed into the recess portion at the lower end of the vacuum tweezer 10 (refer to an upper-right image) while the shape of the donor cornea is temporarily deformed.

Next, when the suturing needle N is driven and moved to penetrate the deformed part of the donor cornea (refer to a lower left image), the suturing yarn T connected to the rear end of the suturing needle N is inserted along the movement path of the suturing needle N and then positioned along the suturing trajectory inside the donor cornea (refer to a lower right image).

Figure 9:
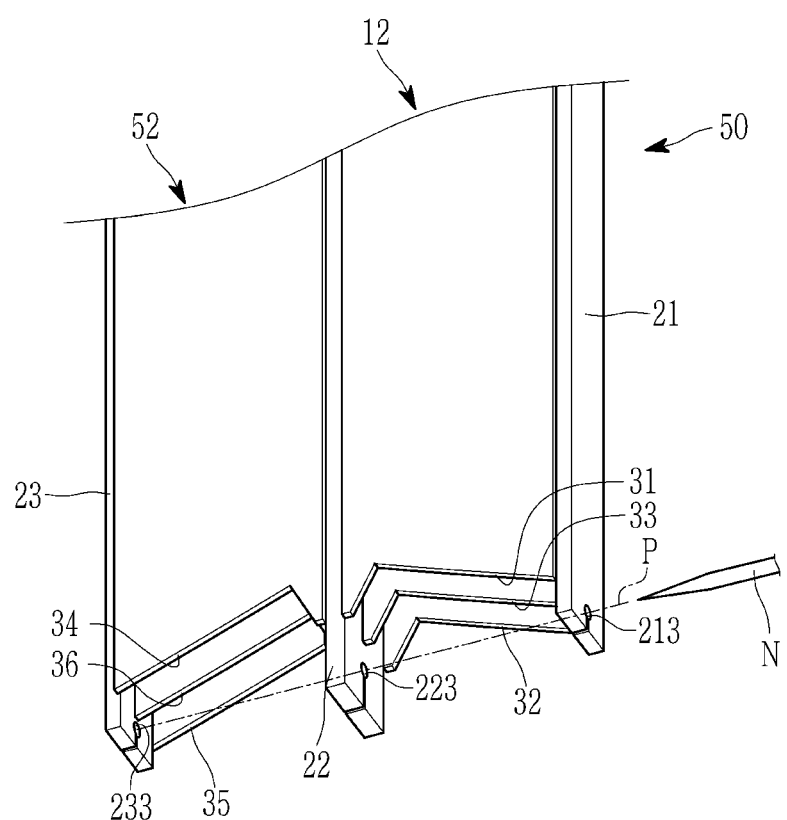
FIG. 9 is a perspective view showing a vacuum tweezer according to another exemplary embodiment of the present invention.
Figure 10:
FIG. 10 is a photographic image showing a state of suturing a cornea by using a tissue suturing device equipped with a vacuum tweezer according to another exemplary embodiment of the present invention.

FIG. 9 is a perspective view showing a vacuum tweezer according to another exemplary embodiment of the present invention, and FIG. 10 is a photographic image showing a state of suturing a cornea by using a tissue suturing device equipped with a vacuum tweezer according to another exemplary embodiment of the present invention.

The vacuum tweezer may be made by combining two or more body members 12 and 52 of the tube shape. Referring to FIG. 9, the vacuum tweezer 50 according to the present exemplary embodiment is made by combining the body members 12 and 52 in the shape of two tubes. That is, the body member 12 of the vacuum tweezer 50 may include a first plate 21, a second plate 22 facing the first plate 21, and a third plate 23 facing the second plate 22. Between the first plate 21 and the second plate 22, the first side plate 31, the second side plate 32, and the third side plate 33 may be connected and fixed to the first plate 21 and the second plate 22, and between second plate 22 and the third plate 23, the fourth side plate 34, the fifth side plate 35, and the sixth side plate 36 may be connected and fixed to the second plate 22 and the third plate 23. Accordingly, the first plate 21 and the second plate 22, and the first side plate 31 and the second side plate 32, may form the first body member 12, and the second plate 22 and the third plate 23, and the third side plate 33 and the fourth side plate 34, may form the second body member 52.

The first plate 21 and the second plate 22 have a first needle hole 213 and a second needle hole 223 that correspond to each other and are penetrated in the part adjacent to the contact end, which is the lower part. Each of the first side plate 31 and the second side plate 32 may have a recess portion that is concave downward at the contact end, and the recess portion may be formed at a higher position than the needle holes 213 and 223. Similarly, in the part adjacent to the contact end of the third plate 23, a third needle hole 233 corresponding to the second needle hole 223 of the second plate 22 is drilled. Accordingly, the first needle hole 213, the second needle hole 223, and the third needle hole 233 may be formed to be positioned on one imaginary needle path line P.

Each of the first side plate 31 and the second side plate 32 may have a recess portion that is concave downward at the contact end, and the recess portion may be formed at a higher position than the needle holes 213 and 223. Similarly, each of the fourth side plate 34 and the fifth side plate 35 may have a recess portion that is concave downward at the contact end, and the recess portion may be formed at a higher position than the needle holes 223 and 233.

The third side plate 33 is positioned between the first side plate 31 and the second side plate 32, and may fix them by connecting the first plate 21 and the second plate 22. In the contact end of the third side plate 33, a recess portion that is concave downward at a position that is higher than the needle holes 213 and 223 may be formed. In addition, the sixth side plate 36 is positioned between the fourth side plate 34 and the fifth side plate 35, and may fix them by connecting the second plate 22 and the third plate 23. A recess portion that is concave downward at the position that is higher than the needle holes 223 and 233 may also be formed at the lower end of the sixth side plate 36.

Each recess portion of the first side plate 31, the second side plate 32, and the third side plate 33 includes a needle path line P connecting the corresponding needle holes 213, 223, and 233, and may be configured to have a profile of the same height with respect to an imaginary plane perpendicular to the first side plate 31 and the second side plate 32. Each recess portion of the fourth side plate 34, the fifth side plate 35, and the sixth side plate 36 includes the needle path line P, and may be configured to have a profile of the same height with respect to an imaginary plane perpendicular to the fourth side plate 34 and the fifth side plate 35.

Here, the recess portion of the first side plate 31 becomes deeper in the direction away from each of the first plate 21 and the second plate 22, and the deepest vertex V of the recess portion may be positioned closer to the second plate 22 than the first plate 21. In addition, the recess portion of the fourth side plate 34 becomes deeper in the direction away from each of the second plate 22 and the third plate 23, and the deepest vertex V of the recess portion may be positioned closer to the second plate 22 than the first plate 21. That is, the first side plate 31 of the first body member 12 and the fourth side plate 34 of the second body member 52 may have recess portions that are symmetrical to each other with respect to the second plate 22.

Also, as above-described, when each recess portion of the second side plate 32 and the third side plate 33 also has the same profile as the first side plate 31, the recess portions of the second side plate 32 and the third side plate 33 also become deeper in the direction away from each of the first plate 21 and the second plate 22, and the deepest vertex V of the recess portion may be positioned closer to the second plate 22 than the first plate 21. Similarly, when the recess portions of the fifth side plate 35 and the sixth side plate 36 also have the same profile as the fourth side plate 34, the recess portions of the fifth side plate 35 and the sixth side plate 36 also become deeper in the direction away from each of the second plate 22 and the third plate 23, and the deepest vertex V of the recess portion may be positioned closer to the second plate 22 than the first plate 21.

The second plate 22 may be configured to extend further downward from the center of the needle hole than the first plate 21 and the third plate 23.

When using the vacuum tweezer 50 according to the present exemplary embodiment configured as described above, it is possible to simultaneously suture a plurality of wounds.

In the above, an example in which the vacuum tweezer is used for corneal suturing has been described, but the vacuum tweezer according to the example may be applied to other parts of the body in addition to the cornea by appropriate morphological modifications, and may also be applied to the suturing of a general wound tissue.

In addition, the vacuum tweezer has the structure in which the lateral cross-section is approximately a rectangle, but it is also possible for the tube-type body member of the vacuum tweezer to have a structure having a lateral cross-section of a different shape such as a circle or an oval, and this is also within the scope of the present invention.

While this invention has been described in connection with what is presently considered to be practical exemplary embodiments, it is to be understood that the invention is not limited to the disclosed embodiments. On the contrary, it is intended to cover various modifications and equivalent arrangements included within the spirit and scope of the appended claims.

DESCRIPTION OF SYMBOLS

10: vacuum tweezer
12: body member
21, 22: first plate, second plate
31, 32, 33: first side plate, second side plate, third side plate
40: needle insertion unit
213, 223: first needle hole, second needle hole
312, 322, 332: recess portion
214, 224: cutout part
N: suturing needle
T: suturing yarn

What is claimed is:

1. A vacuum tweezer comprising:
   a first plate and a second plate of which first and second needle holes facing each other are at lower ends of each of the first and second plates respectively, and are positioned to face each other; and
   a first side plate and a second side plate connecting and fixing the first plate and the second plate to form a tube penetrated upward and downward and including a recess portion that is concave downward at a higher position than an imaginary needle path line connecting the first and second needle holes, respectively,
   wherein the first side plate and the second side plate are disposed higher than the imaginary needle path line from the lower ends of each of the first and second plates.

2. The vacuum tweezer of claim 1, further comprising
   at least one third side plate positioned between the first side plate and the second side plate, connecting and fixing the first plate and the second plate, and including a recess portion that is concave downward at any higher position than the first and second needle holes.

3. The vacuum tweezer of claim 1, wherein
   each recess portion of the first side plate and the second side plate is formed to deepen upward in a direction away from each of the first and second plates.

4. The vacuum tweezer of claim 3, wherein
   a deepest vertex of the recess portions is positioned closer to the second plate than the first plate.

5. The vacuum tweezer of claim 1, wherein
   the length by which the second plate extends downward from the center of the second needle hole is longer than the length by which the first plate extends downward from the center of the first needle hole.

6. The vacuum tweezer of claim 1, wherein
   the second plate has a cutout part extending downward from the second needle hole.

7. The vacuum tweezer of claim 6, wherein
   the width of the cutout part is formed smaller than the diameter of the second needle hole.

8. The vacuum tweezer of claim 1, wherein
   the first plate has a cutout part extending downward from the first needle hole.

9. The vacuum tweezer of claim 8, wherein
the width of the cutout part is formed smaller than the diameter of the first needle hole.

10. The vacuum tweezer of claim 1, further comprising:
a third plate having a third needle hole drilled facing the second needle hole at a lower end, and positioned to face the second plate; and
a fourth side plate and a fifth side plate connecting and fixing the second plate and the third plate to form a tube and including a recess portion that is concave downward at any higher position than the second and the third needle hole at the lower end.

11. A tissue suturing device comprising:
the vacuum tweezer of claim 1;
a needle insertion unit fixed adjacent to one of the first needle hole or the second needle hole of the vacuum tweezer to drive a suturing needle; and
a negative pressure generating unit connected to an upper part of the vacuum tweezer to provide suction power.

* * * * *